United States Patent [19]

Sterzer

[11] Patent Number: 4,967,751
[45] Date of Patent: Nov. 6, 1990

[54] APPARATUS AND METHOD FOR MONITORING THE WAVEFORM OF CYCLIC MOVEMENT WITHIN THE THORAX OF AN INDIVIDUAL

[75] Inventor: Fred Sterzer, Princeton, N.J.

[73] Assignee: MMTC, Inc., Princeton, N.J.

[21] Appl. No.: 190,177

[22] Filed: May 4, 1988

[51] Int. Cl.$^5$ .............................................. A61B 5/113
[52] U.S. Cl. .................................. 128/653 R; 128/721
[58] Field of Search ............... 128/653, 716, 721, 782, 128/670, 671; 324/58.5 R, 58.5 A, 58.5 B; 343/782

[56] References Cited

U.S. PATENT DOCUMENTS 3,483,860  12/1969  Namerow ........................... 128/653
3,993,995  11/1976  Kaplan et al. ....................... 128/721
4,620,146  10/1986  Ishikawa et al. ............... 324/58.5 R
4,638,808   1/1987  Mawhinney ........................ 128/653

Primary Examiner—Ruth S. Smith
Assistant Examiner—K. M. Pfaffle
Attorney, Agent, or Firm—George Seligsohn

[57] ABSTRACT

A carrier-frequency signal transmitted through the individual's thorax from a first module to a second module, is modulated at the second module and retransmitted back through the individual's thorax to the first module. An attribute (e.g., doppler frequency shift or amplitude variation) of solely the modulation component of the signal received by the first module is employed to monitor the waveform of cyclic movement (e.g., breathing rate) within the individual's thorax.

15 Claims, 4 Drawing Sheets

4,967,751

APPARATUS AND METHOD FOR MONITORING THE WAVEFORM OF CYCLIC MOVEMENT WITHIN THE THORAX OF AN INDIVIDUAL

BACKGROUND OF THE INVENTION

1. Field of the Invention

This invention relates to the monitoring of the waveform of cyclic movement, such as the breathing rate and/or the movement of the heart or parts thereof, within the thorax of an individual person or animal (such as a laboratory animal) in accordance with a doppler-shift in frequency of a microwave or radio-frequency signal passing into and out of the thorax of the individual.

2. Description of the Prior Art

The use of doppler-shift radar to monitor the breathing of an individual or, alternatively, in the field of echocardiography is known in the art. Such doppler radar extends from microwave radar scanners that are situated some distance from the individual and pick up reflections off an individual being scanned to doppler radar, operating at a microwave frequency or a lower radio-frequency, which transmits a predetermined-frequency signal into the body of the individual and receives reflections from moving internal organs of the individual. Further, there are known systems which, besides receiving transmitted reflections, also receive microwave signals transmitted through the thorax of an individual from a transmitter located on the opposite side of the thorax from the receiver. In this latter case, both a reference signal corresponding to the microwave signal transmitted into the thorax and the signal received after transmission through the thorax are applied through external wires as respective inputs to the same detector.

In principle, the monitoring of cyclic movement within the thorax of an individual in accordance with a doppler shift in frequency of a microwave or radio-frequency signal can employ either an antenna that is in direct contact with the skin of the individual or an antenna which is not in contact with the skin of the individual. A non-contact receiving antenna picks up scattered energy that follows multitudinous pathways within and around the body. This multipath propagation permits spurious doppler frequency shifts in the received signal arising from motions outside the body of the individual (e.g. motion from another individual or animal in close proximity to the individual, etc.). While direct-contact antennas minimize the scattered radiation problem encountered by non-contact antennas, use of such direct-contact antennas is often infeasible or, at least, undesirable.

One example of a case in which a direct-contact antenna is infeasable is in the monitoring of the breathing rate of an infant (particularly a premature infant) for the purpose of guarding against crib death. Another example is the case of a patient located in a recovery room immediately after the completion of an operation in which the patient has been anesthesized. In such cases, it is not practical to "wire-up" the patient or infant with antennas in direct contact with skin of the individual. Instead, it is much more practical to employ non-contact antennas situated adjacent to the thorax of the individual, such as located within a pocket in a gown or other garment covering the individual.

The present invention provides a practical way of employing non-contact antennas in the monitoring of the waveform of cyclic movement within the thorax or an individual person or animal in accordance with a doppler shift in frequency of a microwave or radio-frequency passing into, through, and then out of the thorax of the individual without being subject to the scattered field produced by moving objects outside the body of the individual.

SUMMARY OF THE INVENTION

In accordance with the principles of the present invention, apparatus is provided for monitoring the waveform of cyclic movement within the thorax of an individual person or animal, which apparatus operates by (1) transmitting a carrier-frequency signal through the thorax of the individual in a first direction to a first receiver; (2) modulating the received carrier-frequency signal at the first receiver with a modulating frequency to derive a modulated carrier-frequency signal; (3) transmitting the modulated carrier-frequency signal back through the thorax of said individual in a second direction opposite to the first direction to a second receiver; and (4) monitoring an attribute of the waveform of solely the modulation component of the modulated carrier-frequency signal received at the second receiver.

An additional feature of the present invention is that it permits all of the essential elements of the apparatus of the present invention to be housed entirely within two (small) battery-powered modules (one of which may be positioned adjacent to the chest of an individual being monitored and the other of which maybe positioned adjacent to the back of the individual being monitored), thereby requiring no external wiring.

DESCRIPTION OF PREFERRED EMBODIMENTS

Figure 1:
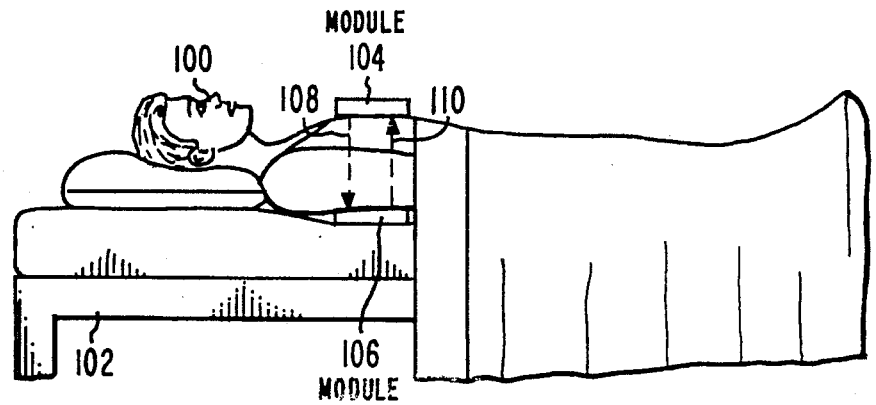
FIG. 1 is an illustrative showing of a post-operative patient lying on a bed within a recovery room, with the patient having a first battery-energized module adjacent to his chest and a second battery-energized module adjacent to his back.

For illustrative purposes in describing the invention, it is assumed that the present invention is employed in monitoring the breathing rate of a post-operative patient who has been placed in a recovery room while the patient is coming out of general anesthesia. More specifically, as shown in FIG. 1, patient 100, lying on a bed or stretcher 102, has a first module 104 positioned adjacent a point (e.g. the center) of the chest of patient 100 and has a second module 106 positioned adjacent a point opposite module 104 of the back of patient 100. First module 104 and second module 106 need not be attached to the body of patient 100, but are preferably situated in pockets sewn onto a hospital gown worn by patient 100.

Figure 2:
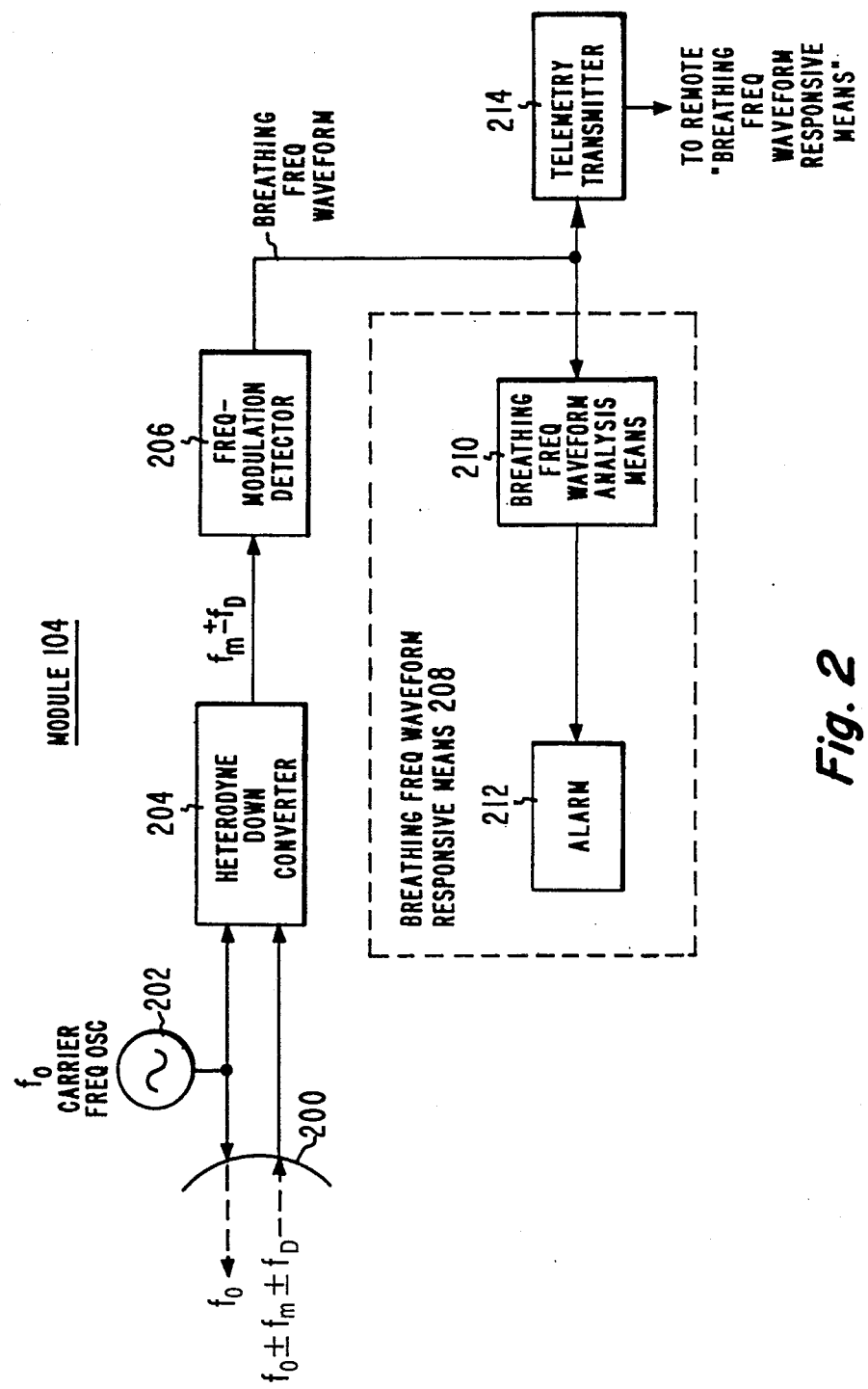
FIG. 2 is a block diagram of an embodiment of that portion of the apparatus of applicant's invention that is incorporated in the first module shown in FIG. 1.

First battery-energized module 104 incorporates the structure shown in FIG. 2, together with a battery-operated power supply therefore, which is not shown in FIG. 2. Second battery-energized module 106 incorporates the structure shown in FIG. 3, together with a battery-operated power supply therefor, which is not shown. Thus, as indicated in FIG. 1, there are no external wires connected to either first module 104 or second module 106 for any purpose whatsoever. Instead, first module 104 transmits a first signal through the body of patient 100 to the second module 106 in one direction (as indicated by arrow 108) and second module 106 in response thereto, retransmits a second signal back through the body of patient 100 to first module 104 in an opposite direction (as indicated by arrow 110). The fact that neither modules 104 nor 106 need be attached to the body of patient 100 and, in addition, require no external wires, is considered to be one of the desirable features of the present invention. However, the battery energization of modules 104 and 106, while desirable, is not essential to the present invention.

Referring to FIG. 2, there is shown the structure (other than the battery-operated power supply therefor) of first module 104. Specifically, this structure includes antenna 200, carrier-frequency oscillator 202, operating at a carrier-frequency of $f_o$, heterodyne down-converter 204, frequency-modulation detector 206, breathing-frequency waveform responsive means 208 (which includes breathing-frequency waveform analysis means 210 and alarm 212), and telemetry transmitter 214. Antenna 200, which is preferably a microstrip antenna, is situated in the front of first module 104, facing the body of the patient. Carrier-frequency $f_o$ from oscillator 202 is applied both as a transmitting signal to antenna 200 and as a first input to heterodyne down-converter 204. The carrier-frequency is preferably a radio-frequency signal, such a 40 MHz., by way of example, althought it also may be a microwave signal. The signal transmitted back to first module 104 from second module 106 is received by antenna 200 and applied as a second input to heterodyne down-converter 204.

The output from heterodyne down-converter 204 is applied as an input to frequency-modulation detector 206. The output from frequency-modulation detector 206 is applied as an input both to breathing frequency waveform analysis means 210 of breathing-frequency waveform responsive means 208 and to telemetry transmitter 214. The output of breathing-frequency waveform analysis means 210 is supplied as an input to alarm 212 of breathing-frequency waveform responsive means 208.

Figure 3:
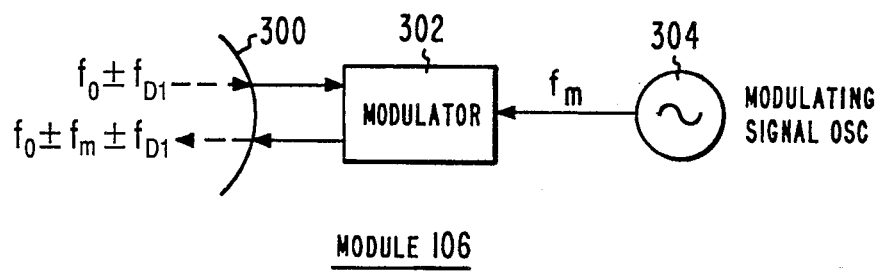
FIG. 3 is a block diagram of an embodiment of a portion of the apparatus of applicant's invention that is incorporated in the second module shown in FIG. 1.

Referring to FIG. 3, second module 106, besides including a battery-operated power supply (not shown), incorporates antenna 300, modulator 302 and modulating signal oscillator 304, which operates at a frequency $f_m$.

Antenna 300, which may be a microstrip antenna, is situated in the front of second module 106 facing the back of the patient. Antenna 300, which receives the carrier-frequency signal transmitted from antenna 200 of first module 104 through the body of the patient, supplies the received signal as the first input to modulator 302. Modulating signal $f_m$ (which may have a frequency of about 50 kHz) is applied as a second input to modulator 302, and the modulated output from modulator 302 is applied as an input to antenna 300, which transmits this modulated signal back through the body of a patient to antenna 200 of first module 104.

Considering now the operation of the present invention, only a portion of the carrier-frequency $f_o$ signal energy transmitted from antenna 200 of first module 104 reaches antenna 300 of second module 106, and is received thereby. Some of the remainder of the transmitted carrier-frequency $f_o$ signal energy is back-scattered by organs of the patient's body and received by antenna 200 of first module 104. In addition, since antenna 200 is not in contact with the patient's body, a portion of the carrier-frequency $f_o$ signal energy transmitted by antenna 200 travels outside of the patient's body. Some of this outside-traveling carrier-frequency $f_o$ signal energy, as well as some of the carrier-frequency $f_o$ signal energy that has passed through and then beyond the patient's body, will be back-scattered by objects outside the patient's body and be received by antenna 200. This received back-scattered energy will include a doppler-frequency component. Some of this doppler-frequency component is caused by such cyclic movement of and within the patient's body as the patient's breathing rate, the beating rate of the patient's heart, movement of the heart's valves, etc. In addition, some of the doppler component in the back-scattered energy received by antenna 200 can arise from the breathing rate of another person standing near the patient, etc.

It is plain that the apparatus for monitoring such cyclic movement as the breathing rate of a patient in a recovery room cannot tolerate any false positives. If the patient's breathing rate becomes abnormal it is essential that the apparatus actuate an alarm with no margin for error. However, in the case of the back-scattered energy received by antenna 200, doppler components thereof rising from cyclic motion outside the patient's body can mask the fact that the patient's breathing rate has become abnormal. In this latter case, a false positive, caused by the cyclic movement outside the patient's body, could be interpreted as normal patient breathing and prevent actuation of an alarm, resulting in drastic consequences for the patient.

The present invention prevents such false positives from occurring. More specifically, only that particular portion of the originally transmitted carrier-frequency $f_o$ signal energy from antenna 200 of first module 104 that (1) passes through the body of the patient, (2) reaches and is received by antenna 300 of second module 106 (3) is modulated by modulating frequency $f_m$ and (4) is then retransmitted from antenna 300 back through the body of the patient and is received by antenna 200 first module 104, is employed for monitoring the patient's breathing rate.

As shown in FIG. 3, due to the breathing motion of the thorax of the patient, the frequency of the signal received by antenna 300 is doppler-shifted by an amount $f_o$ in its passage from antenna 200 of first module 104 through the thorax of the patient to antenna 300 of second module 106. More specifically, movement due to inhaling results in a lowering of the carrier-frequency $f_o$ by the doppler-frequency $f_{D1}$, while exhaling results in an increase in the carrier-frequency $f_o$ by doppler-frequency $f_{D1}$. Thus, as indicated in FIG. 3, the frequency of the signal received by antenna 300 is "$f_o \pm f_{D1}$". After modulation by modulating frequency $f_m$, the retransmitted frequency from antenna 300 includes an upper sideband "$f_o+f_m\pm f_{D1}$" and a lower sideband "$f_o-f_m\pm f_{D1}$".

The retransmitted signal is further doppler shifted during its trip back from antenna 300 of module 106 through the thorax of the patient to antenna 200 of first module 104. The round-trip doppler-shift is $f_D$. Therefore, antenna 200 of first module 104 receives a signal which includes an upper sideband $f_o+f_m\pm f_D$ and a lower sideband $f_o-f_m\pm f_D$.

The heterodyning of the desired modulation component of the signal received by antenna 200 is heterodyned with carrier-frequency $f_o$ in down-converter 204 to derive, as an output, the modulating frequency $f_m$ frequency-modulated by doppler-frequency $f_D$ (designated $f_m\pm f_D$ and shown in the timing diagram of FIG. 4, discussed below). However, heterodyning of the undesired back-scattered component (discussed above) of the signal received by antenna 200 with carrier-frequency $f_o$ results in a baseband doppler-frequency $f_D$, per se (rather than the derived frequency-modulation component $f_m\pm f_D$). The output portion of heterodyne down-converter 204 includes a filter which passes $f_m\pm f_D$, but rejects baseband $f_D$.

Frequency-modulation detector 206 demodulates the frequency-modulated input thereto, and derives a breathing frequency waveform (shown in the FIG. 5 timing diagram, discussed below).

Figure 4:
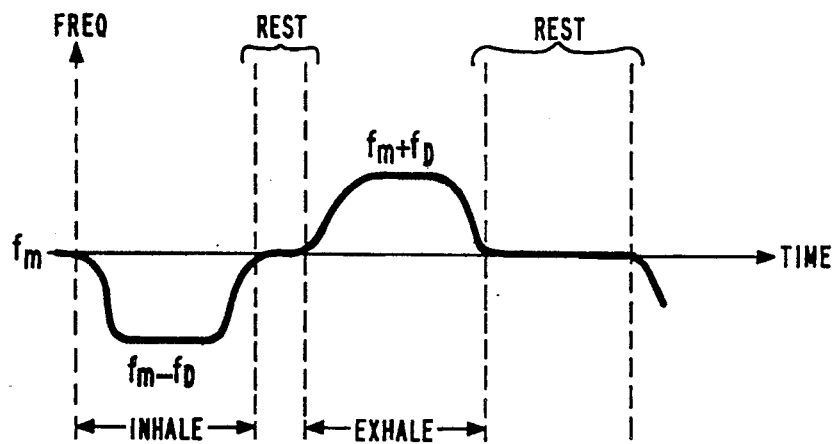
FIGS. 4 and 5 are illustrative timing diagrams showing, by way of example, the breathing-cycle waveform of the patient shown in FIG. 1, which waveform is being monitored by applicant's invention.

Referring to FIG. 4, there is shown a simplified plot of frequency as a function of time for the output from heterodyne down-converter 204. This simplified plot is limited to showing the effect of the breathing rate of the patient. Therefore, in FIG. 4, the effect of other types of cyclic movement in the thorax of the patient, such as movement of the patient's heart and parts thereof, which occur in practice, have been ignored. As shown in FIG. 4, as the patient inhales from an original rest position, (so that the distance between his chest and his back is expanding), the frequency $f_m$ at rest decreases to a frequency $f_m-f_D$ determined by the velocity of expansion, and then falls back to $f_m$ when the inhale expansion has reached its maximum point. The patient remains at rest at this maximum expansion point for a short time and then begins to exhale. During an exhale, the distance between the patient's chest and back contracts, resulting in an increase in frequency. More particularly, the frequency rises from the rest frequency $f_m$ to $f_m+f_D$, which occurs at the maximum velocity of contraction, and then falls back to $f_m$ when the contraction is completed at the end of the exhale. The patient then remains at rest for a relatively long interval before beginning his next breathing cycle.

Figure 5:
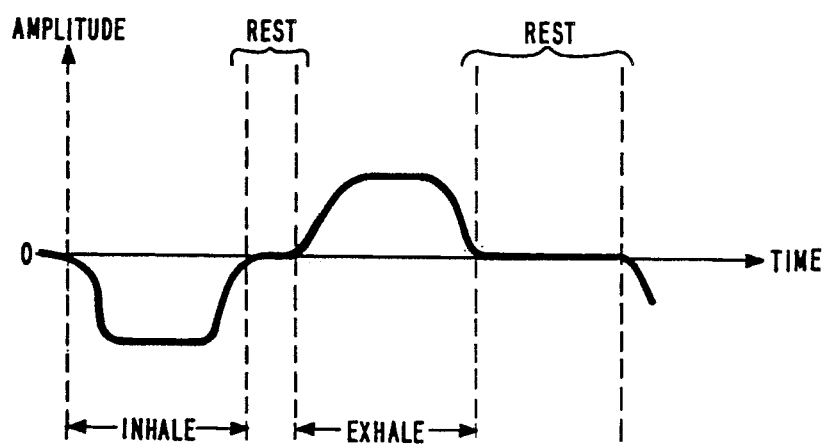

As indicated in FIG. 5, demodulation of the frequency-modulated signal by frequency-modulation detector 206 does not result in a change in the shape of the waveform shown in FIG. 4, but merely substitutes, in FIG. 5, amplitude as a function of time for frequency as a function of time, as shown in FIG. 4.

Returning to FIG. 2, the breathing-frequency waveform at the output of frequency-modulation detector 206 is applied as an input to breathing-frequency waveform analysis means 210 of breathing-frequency waveform responsive means 208, as well as being applied as an input to telemetry transmitter 214. Telemetry transmitter 214 transmits a signal defining the breathing-frequency waveform to a remote breathing-frequency waveform responsive means (which may be located at a nurse's station, for instance).

As discussed above, the breathing frequency waveforms shown in FIGS. 4 and 5 are simplified compared to those actually found in practice. Actually the breathing-frequency waveform is a complex waveform having a fundamental frequency component (determined in accordance with the number of zero-crossings per unit time) defining the breathing rate. The complex waveform also includes superimposed lower-amplitude, higher-frequency components corresponding to the waveforms of cyclic movement of the heart and its parts. In addition, the cyclic change in the distance between antennas 200 and 300 caused by the patient's breathing also results in changes in the impedence presented by antenna 200. Such changes in impedence affect the shape of the breathing frequency waveform.

The breathing-frequency waveform analysis means 210 includes such elements as filters, a priori stored empirical data and/or computational means for (1) separating or removing heart-frequency components from breathing-frequency components of the complex waveform, and (2) determining whether the breathing of the patient and/or the heart rhythm of the patient is normal or abnormal. For instance, besides indicating breathing-frequency, integration as a function of time of each of the inhale and/or exhale portions of the breathing frequency waveform would provide an indication of whether or not the breathing of the patient was shallow.

The data available at the output of breathing-frequency waveform analaysis means 210 provides an indication of whether the breathing and/or heart rhythm of the patient is normal or is abnormal. Alarm 212 provides an indication (e.g., sound, flashing lights, etc.) of an abnormal condition of the patient. Preferably, alarm 212 is designed to be in a normally actuated state and is deactuated only in response to the data output from breathing-frequency waveform analysis means 210 that is applied as input thereto indicating that the patient's breathing and/or heart rhythm is normal. This would provide a fail-safe operation of alarm 212.

As shown in FIG. 2, there are both a local breathing frequency waveform responsive means 208 and a telemetry transmitter 214 for transmitting to a remote breathing frequency waveform responsive means. Furthermore, telemetry transmitter 214 transmits data relating to the breathing frequency waveform obtained from frequency modulation detector 206 that is applied as an input to frequency waveform analysis means 210. Variations of this scheme are within the contemplation of the present invention. It is possible to provide a system which employs either a local or remote breathing frequency waveform responsive means 208, but not both. Obviously, if there is not to be a remote breathing frequency waveform responsive means, there is no need for telemetry transmitter 214. Also, it is possible to employ only a remote alarm and, in this case, employ a telemetry transmitter which transmits only the data at the output of breathing frequency waveform analysis means 210 to the remote alarm.

Although for illustrative purposes, the present invention has been described assuming that the individual being monitored is a post-operative patient in a recovery room, it is apparent that any type of cyclic movements within the thorax of both people and animals can be monitored by the present invention. For instance, the present invention is particularly applicable to monitoring the breathing rate of infants (including premature infants) that are subject to sudden crib death.

It is also apparent that the position of the first and second modules can be reversed; that is, the first module 104 could be positioned adjacent the back of the patient in FIG. 1, and the second module 106 could be positioned adjacent the chest of the patient in FIG. 1.

The present invention may take other forms than those specifically described above. For instance, a nurse may wish to monitor the breathing rate of each of respective patients with portable apparatus. In this case, the second module may be situated permanently in the patient's mattress in the vicinity of the thorax (chest or back) of each patient. The nurse by situating a portable first module above the patient in the vicinity of the patient's thorax can read the breathing rate of the patient from a meter incorporated in the waveform responsive means of the first module.

Figure 2A:
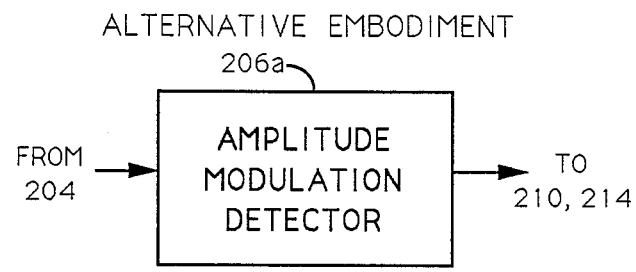
FIG. 2a illustrates a modification of the FIG. 2 structure that results in an alternative embodiment of the apparatus of the present invention.

Furthermore, as brought out above, the impedance presented by antenna 200 changes in accordance with cyclic changes in distance between antennas 200 and 300 due to the patient's breathing. The amplitude of the output signal from converter 204 varies in accordance with changes in this impedance. Therefore, in an alternative embodiment of the present invention, shown in FIG. 2a, an amplitude detector 206a, substituted for frequency-modulation detector 206, would provide a breathing frequency waveform that defines the expansion and contraction of the thorax of the patient due to breathing.

What is claimed is:

1. In apparatus for monitoring the waveform of cyclic movement within the thorax of an individual person or animal; wherein said apparatus comprises (a) a first antenna adapted to be positioned in the vicinity of a point on the chest of said individual, (b) a second antenna adapted to be positioned in the vicinity of of a point on the back of said individual, (c) first means coupled to one of said first and second antennas for transmitting a carrier signal having a frequency $f_0$ from said one of said first and second antennas to the other of said first and second antennas through the thorax of said individual, whereby said other of said first and second antennas receives said transmitted carrier signal, (d) second means coupled to said other of said first and second antennas for transmitting a return signal through the thorax of said individual back to said one of said first and second antennas, whereby said one antenna receives a signal comprised of separate components derived respectively from said return signal transmitted from said other antenna and from back-scatter of said carrier signal transmitted from said one antenna, and (e) heterodyne down-converter means for subtracting said frequency $f_0$ from said signal receive by one of said first and second antennas the improvement wherein:

said second means includes means for modulating said signal received by said other of said first and second antennas with a modulating frequency $f_m$ prior to transmitting said return signal through the thorax of said individual back to said one of said first and second antennas, whereby solely the return-signal derived component of said signal received by said one antenna includes said frequency $f_0$ modulated by a frequency $(f_m \pm f_D)$, where $f_D$ is a doppler frequency component which frequency-modulates $f_m$ in accordance with said cyclic movement within said thorax;

said heterodyne down-converter means including means for selectively deriving an output which has said frequency $(f_m \pm f_D)$ and an amplitude both of which vary in accordance with said cyclic movement within said thorax, but which selectively-derived output excludes down-converted baseband frequencies, whereby the down-converted backscatter component is substantially absent from said said selectively-derived output of said heterodyne down-converter means; and detector means for detecting said output of said heterodyne down-converter means for deriving a waveform that defines a given attribute of said cyclic movement within said thorax as a function of time.

2. The apparatus defined in claim 1, further comprising:

waveform-responsive means for analyzing said waveform from said detector means to determine whether or not said waveform corresponds to an abnormal condition of said individual, said waveform-responsive means including an alarm that is actuated whenever said abnormal condition has been determined to exist.

3. The apparatus defined in claim 2, wherein:

said alarm is normally actuated, and said waveform-responsive means includes means for deactuating said alarm only in response to said analyzed waveform corresponding to a normal condition of said individual.

4. The apparatus defined in claim 2, wherein said cyclic movement within said thorax includes the breathing rate of said individual; and wherein:

said waveform-responsive means includes means responsive to the fundamental frequency of said waveform from said detector means, and means for determining that an abnormal condition exists whenever the number of cycles of said fundamental frequency per unit time is outside of a range having a predetermined minimum value and a predetermined maximum value.

5. The apparatus defined in claim 4, wherein said cyclic movement within said thorax further includes movements of the heart of said individual, and wherein:

said waveform from said detector means is a complex wave comprised of a relatively low-frequency component determined by said breathing rate of said individual and a relatively high-frequency component determined by the movements of said heart of said individual superimposed on said relatively low-frequency component; and said means responsive to said waveform from said detector means includes filter means for separating said relatively high and relatively low frequency components from one another.

6. The apparatus defined in claim 2, further comprising first and second modules; wherein:

said first module incorporates as elements therein (1) said one of said first and second antennas, (2) said first means, (3) said heterodyne down-converter means, (4) said detector means, (5) said waveform-responsive means, and (6) a first battery-operated power supply for energizing all elements incorporated in said first module; and said second module incorporates as elements therein (7) said other of said first and second antennas, (8) said second means, and (9) a second battery-operated power supply for energizing all elements incorporated in said second module.

7. The apparatus defined in claim 6, wherein said first module further incorporates telemetry means for transmitting waveform data to a remote location.

8. Apparatus defined in claim 1, further comprising first and second modules; wherein;
  said first module incorporates as elements therein (1) said one of said first and second antennas, (2) said first means, (3) said heterodyne down-converter means, (4) said detector means, and (5) a first battery-operated power supply for energizing all elements incorporated in said first module; and
  said second module incorporates as elements therein (6) said other of said first and second antennas, (7) said second means, and (8) a second battery-operated power supply for energizing all elements incorporated in said second module.

9. The apparatus defined in claim 8, wherein said first module further incorporates telemetry means for transmitting waveform data to a remote location.

10. The apparatus defined in claim 1, wherein:
  said carrier-signal frequency $f_o$ is a radio-frequency signal.

11. The apparatus defined in claim 1, wherein:
  said detector means comprises a frequency-modulation detector for deriving a waveform that defines the velocity of said cyclic movement within said thorax as a function of time.

12. The apparatus defined in claim 1, wherein:
  said detector means comprises an amplitude detector for deriving a waveform that defines changes in impedance of said one of said first and second antennas due to said cyclic movement within said thorax as a function of time.

13. In a method for monitoring the waveform of an attribute of cyclic movement within the thorax of an individual person or animal in accordance with a carrier-frequency signal passing into and out of the thorax of said individual; the improvement comprising the steps of:
  transmitting said carrier-frequency signal through the thorax of said individual in a first direction to a first receiver;
  modulating said received carrier-frequency signal at said first receiver with a modulating frequency to derive a modulated carrier-frequency signal;
  transmitting said modulated carrier-frequency signal back through the thorax of said individual in a second direction opposite to said first direction to a second receiver; and
  monitoring the waveform of solely said attribute of the modulation of the modulated carrier-frequency signal received at said second receiver.

14. The method defined in claim 13, wherein the step of monitoring comprises the step of:
  monitoring the waveform of a doppler shift in frequency of the modulated carrier-frequency signal due to said cyclic movement.

15. The method defined in claim 13, wherein the step of monitoring comprises the step of:
  monitoring the waveform of changes in an amplitude of said modulation component of the modulated carrier-frequency signal due to said cyclic movement.

* * * * *